United States Patent
McNichols et al.

(10) Patent No.: US 7,027,859 B1
(45) Date of Patent: *Apr. 11, 2006

(54) ELECTROTRANSPORT DELIVERY DEVICE HAVING IMPROVED SAFETY AND REDUCED ABUSE POTENTIAL

(75) Inventors: Larry A. McNichols, Coon Rapids, MN (US); John D. Badzinski, Coon Rapids, MN (US); William N. Reining, Cross Plains, WI (US); Gary A. Lattin, Forest Lake, MN (US); Ronald P Haak, Menlo Park, CA (US); Joseph B. Phipps, Plymouth, MN (US)

(73) Assignee: ALZA Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/312,336

(22) Filed: Sep. 26, 1994

(51) Int. Cl.
*A61N 1/30* (2006.01)

(52) U.S. Cl. .......................... 604/20; 604/110
(58) Field of Classification Search ............ 604/20–21; 2/110; 607/152, 63
See application file for complete search history.

(56) References Cited

U.S. PATENT DOCUMENTS

| 3,493,657 | A | 2/1970 | Lewenstein |
| 3,773,955 | A | 11/1973 | Pachter et al. ............. 424/260 |
| 4,141,359 | A | 2/1979 | Jacobsen et al. ......... 128/172.1 |
| 4,457,933 | A | 7/1984 | Gordon et al. ............. 424/260 |
| 4,474,570 | A | 10/1984 | Ariura et al. ................. 604/20 |
| 4,588,580 | A | 5/1986 | Gale et al. .................... 424/21 |
| 4,731,926 | A | 3/1988 | Sibalis ......................... 29/877 |
| 4,942,883 | A | 7/1990 | Newman ..................... 128/798 |
| 5,006,108 | A | 4/1991 | LaPrade ...................... 604/20 |
| 5,037,381 | A | 8/1991 | Bock et al. .................. 604/20 |
| 5,047,007 | A | 9/1991 | McNichols .................. 604/20 |
| 5,135,477 | A | 8/1992 | Untereker et al. ............ 604/20 |
| 5,135,479 | A | 8/1992 | Sibalis et al. ................ 604/20 |
| 5,147,297 | A | 9/1992 | Myers et al. ................. 604/20 |
| 5,160,316 | A * | 11/1992 | Henley ........................ 604/20 |
| 5,167,617 | A | 12/1992 | Sibalis ........................ 604/20 |

(Continued)

FOREIGN PATENT DOCUMENTS

| GB | 2239803 A | 7/1991 |
| WO | WO9407566 | 4/1994 |

*Primary Examiner*—Mark Bockelman

(57) ABSTRACT

An electrotransport device (20) for delivering one or more therapeutic agents through the skin includes electrodes (30, 32) for contacting the skin (34), at least one electrode containing the agent, a power source (22) for generating electrical current ($I_L$) for delivering the agent, a current generating and controlling means (24), and a disabling means (26) for permanently and irreversibly disabling the current. The disabling means (26) may include a timer means (66), a counter means (82), or a body parameter sensor (134) and limit comparator (132) to effect permanent disabling. The disabling means may be a permanent transition to a disabled logic state, a permanent discharge of a power supply source (22), or a permanent diversion of electrotransport current from the electrodes (30,32), or a combination of the above. The permanent disabling means may include a circuit connection means (304,308,326,328) having a frangible conducting member (332) which permanently fractures and causes an irreversible open circuit in the connection to the electrodes (334,342) upon removing a disposable/single use electrode assembly (300) from a reusable portion of an electrotransport device.

17 Claims, 7 Drawing Sheets

U.S. PATENT DOCUMENTS

| | | |
|---|---|---|
| 5,203,768 A | 4/1993 | Haak et al. .................... 604/20 |
| 5,224,927 A | 7/1993 | Tapper ........................ 604/20 |
| 5,224,928 A | 7/1993 | Sibalis et al. ................. 604/20 |
| 5,232,438 A | 8/1993 | Theeuwes et al. ............. 604/20 |
| 5,246,418 A | 9/1993 | Haynes et al. ................ 604/20 |
| 5,254,081 A | 10/1993 | Maurer et al. ................ 604/20 |

* cited by examiner

ELECTROTRANSPORT DELIVERY DEVICE HAVING IMPROVED SAFETY AND REDUCED ABUSE POTENTIAL

TECHNICAL FIELD

This invention relates to electrotransport devices for delivering a therapeutic agent (eg., a drug), which devices have improved safety and reduced potential for abuse. In particular, the devices of this invention are intended to administer the agent to the body by electrotransport through the skin or mucosa.

BACKGROUND ART

The term "electrotransport" as used herein refers generally to the delivery of an agent (eg, a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid. The liquid contains the agent to be delivered, under the influence of an electric field. Still another type of electrotransport process, electroporation, involves the formation of transiently-existing pores in a biological membrane by the application of an electric field. An agent can be delivered through the pores either passively (ie, without electrical assistance) or actively (ie, under the influence of an electric potential). However, in any given electrotransport process, more than one of these processes may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, regardless of the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, ie, a cation, then the anode is the active or donor electrode, while the cathode serves to complete the circuit. Alternatively, if an agent is negatively charged, ie, an anion, the cathode is the donor electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Furthermore, passive flux control membranes, adhesives for maintaining device contact with a body surface, insulating members, and impermeable backing members are some other potential components of an electrotransport device.

All electrotransport agent delivery devices utilize an electrical circuit to electrically connect the power source (eg, a battery) and the electrodes. In very simple devices, such as those disclosed by Ariura et al in U.S. Pat. No. 4,474,570, the "circuit" is merely an electrically conductive wire used to connect the battery to an electrode. Other devices use a variety of electrical components to control the amplitude, polarity, timing, waveform shape, etc. of the electric current supplied by the power source. See, for example, U.S. Pat. No. 5,047,007 issued to McNichols et al.

To date, commercial transdermal iontophoretic drug delivery devices (eg, the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a bio-compatible electrolyte salt. The "satellite" electrodes are connected to the electrical power supply unit by long (eg, 1–2 meters) electrically conductive wires or cables. Examples of desk-top electrical power supply units which use "satellite" electrode assemblies are disclosed in Jacobsen et al U.S. Pat. No. 4,141,359 (see FIGS. 3 and 4); LaPrade U.S. Pat. No. 5,006,108 (see FIG. 9); and Maurer et al U.S. Pat. No. 5,254,081 (see FIGS. 1 and 2).

More recently, small self-contained electrotransport delivery devices adapted to be worn on the skin, sometimes unobtrusively under clothing, for extended periods of time have been proposed. The electrical components in such miniaturized iontophoretic drug delivery devices are also preferably miniaturized, and may be in the form of either integrated circuits (ie, microchips) or small printed circuits. Electronic components, such as batteries, resistors, pulse generators, capacitors, etc. are electrically connected to form an electronic circuit that controls the amplitude, polarity, timing waveform shape, etc. of the electric current supplied by the power source. Such small self-contained electrotransport delivery devices are disclosed for example in Tapper U.S. Pat. No. 5,224,927; Haak et al U.S. Pat. No. 5,203,768; Sibalis et al U.S. Pat. No. 5,224,9928; and Haynes et al U.S. Pat. No. 5,246,418. One concern, particularly with small self-contained electrotransport delivery devices which are manufactured with the drug to be delivered already in them, is the potential loss in efficacy after a long period of device storage. In an electrotransport device using batteries and other electronic components, all of the components have various shelf lives. If it is known, for example, that the batteries used to power these small delivery devices will gradually degrade, and the drug delivery rate may go off specification. It would be advantageous to have a means to limit the active life of the delivery device for a certain period of time (eg, months) after device manufacture in order to prevent this potential loss in device efficacy.

Application of therapeutic drugs, whether by electrotransport or more traditional (eg, oral) dosing, can sometimes cause unwanted reactions in certain patients. These reactions can take many forms, including change in heart rate, change in body temperature, sweating, shaking and the like. It would be advantageous to automatically and permanently disable an electrotransport drug delivery device upon encountering such "unwanted" reactions.

The potential for abuse by either oral or parenteral routes of narcotic and other psychoactive drugs is well known. For example, the potential for abuse of the synthetic narcotic drug fentanyl is so high that it has become a major cause of death for anesthesiologists and other hospital workers having access to the drug. In order to prevent abuse of these substances, it has been proposed to provide dosage forms which combine the abusable substance with an amount of an antagonist for the abusable substance sufficient to eliminate the "high" associated with abuse of the substance without eliminating the other therapeutic benefits for which the drugs are intended to be administered. See, for example, U.S. Pat. Nos. 4,457,933; 3,493,657; and 3,773,955 which are incorporated herein by reference.

Many abusable substances are capable of being administered to the body by direct application of the drug to the skin or mucosa, ie, nasal, vaginal, oral, or rectal mucosa. See for example Gale et al U.S. Pat. No. 4,588,580. They can also be delivered to the body by electrotransport. See Theeuwes et al U.S. Pat. No. 5,232,438 which is incorporated herein by reference. Electrotransport devices which are intended to deliver an abusable drug, such as a narcotic analgesic pain killing drug, could be subject to abuse.

Depending on the level of drug delivery that a particular patient needs in order to control pain, there may be a significant amount of drug left in a delivery device when it is discarded. When a conventional electrotransport device is discarded, it can be retrieved and reapplied (ie, by an abuser) in order to deliver the remaining drug.

It would clearly be desirable to have such devices available in a condition in which the abuse potential of the device is reduced without diminishing the intended therapeutic efficacy of the device or the abusable substance to be administered.

DISCLOSURE OF INVENTION

It is an object of the present invention to provide a device and method, for administering a drug through a body surface (eg, skin) by electrotransport, having improved safety, efficacy and certainty of drug delivery according to pre-established specifications.

It is a further object of this invention to provide a device and method for administering an abusable substance to the body by electrotransport, which device and method have a lower potential for abuse.

The present invention provides an electrotransport device, and a method of operation thereof, which have automatic and irreversible current disabling means to satisfy the above needs.

The present invention provides an electrotransport agent delivery device and a method of operating same. The device includes a pair of electrodes, at least one of the electrodes containing the agent to be delivered, a source of electrical power adapted to be electrically connected to the pair of electrodes, a circuit means electrically connected to the pair of electrodes and a current generating circuit including a source of electrical power for generating an electric current output for delivering the agent by electrotransport. The improved method includes automatically and irreversibly disabling the current output of the current generating circuit after the occurrence of a predetermined event. The present invention encompasses a number of different embodiments which automatically and irreversibly disable the current output upon one or more of the predetermined events mentioned immediately below.

One embodiment of this invention provides a timer to initiate a permanent and irreversible disabling means. This allows permanent and irreversible disabling of the delivery current after either (i) a predetermined short period of time (eg, an hour or a day), (ii) a predetermined intermediate period of time (eg, several days or week(s)), or (iii) a predetermined longer period of time (eg, months or years after manufacture of the device).

Another embodiment of this invention provides a counter to count the number of doses delivered and to permanently disable the electrotransport device after delivery of a predetermined number of doses. This allows the disabling of the device to occur before the depletion of the therapeutic agent apportioned in a predetermined number of doses.

Yet another embodiment of this invention provides a means for permanently disabling the delivery current when the current has been interrupted for a significantly long period of time after first initiation of delivery. This allows for permanently disabling the device once the device is removed from the intended patient and prevents later use (eg, abuse) by an unauthorized person.

A further embodiment of this invention provides a means for permanently disabling the delivery current when a sensed body parameter exceeds some predetermined limit.

A still further embodiment of this invention provides a means for permanently disabling the operability of a disposable and/or single use drug-containing component of an electrotransport delivery device having a reusable component which is adapted to be used with multiple disposable and/or single use drug-containing components. The disposable/single use component is permanently disabled by breaking a frangible electrical circuit connection. The frangible electrical circuit connection is automatically broken when the disposable/single use component is disconnected from the reusable component.

A still further embodiment of this invention comprises a circuit having a conducting member comprised of a material which is electrically conductive but which is electrochemically consumed during a predetermined period of operation of the device. Once the material is electrochemically consumed, the circuit is either broken or the voltage is significantly altered so that a sensor can sense that the material is consumed and generate a disabling signal which permanently and irreversibly disables the device. Preferably either a timer, in the case of an electrotransport device which applies a constant level of current, or a current integrator, in the case of an electrotransport device which applies a level of current which varies over time, is also provided to turn off the device after a predetermined period of time has passed, or a predetermined amount of charge has been transferred to the patient. In this manner, the timer or current integrator acts as a primary means for disabling the current output of the device while the electrochemically consumable material acts as a secondary or back-up means for disabling the current output of the device.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein.

MODES FOR CARRYING OUT THE INVENTION

The present invention relates generally to apparatus (eg, electrical circuits) which are used to enhance the safety and efficacy of electrotransport drug delivery. In one particular example, where the drug being delivered by electrotransport is an abusable drug (eg, a narcotic analgesic), the present invention enhances safety by limiting the potential for unauthorized use of the electrotransport delivery device. The abuse potential that this particular embodiment of the invention is intended to reduce is not the abuse potential associated with the use of the drug reservoir compositions by modes of administration other than electrotransport (eg, injection or ingestion of the drug taken from the drug reservoir of the electrotransport device). Instead, the abuse potential referred to herein relates to the illicit, nonprescription or recreational use of the electrotransport device of this invention in the same mode of administration as intended for its therapeutic use. Drugs having particular potential for abuse include natural and synthetic narcotics and other psychoactive substances. Representative of such substances are, without limitation, analgesic agents such as fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine.

Those skilled in the art of electrotransport drug delivery will readily appreciate that the present invention has significantly broader use than just limiting the potential for unauthorized use/abuse. For example, the invention can be used to ensure that only those electrotransport delivery devices which are operated within a predetermined shelf life, and therefore are still efficacious, can be used. The invention can also be used to disable the electrotransport delivery device before depletion of drug within the drug reservoir of the device in order to ensure that the drug delivery rate remains on specification. The invention can also be used to automatically terminate electrotransport drug delivery in those patients experiencing unwanted reactions to the drug.

Figure 1:
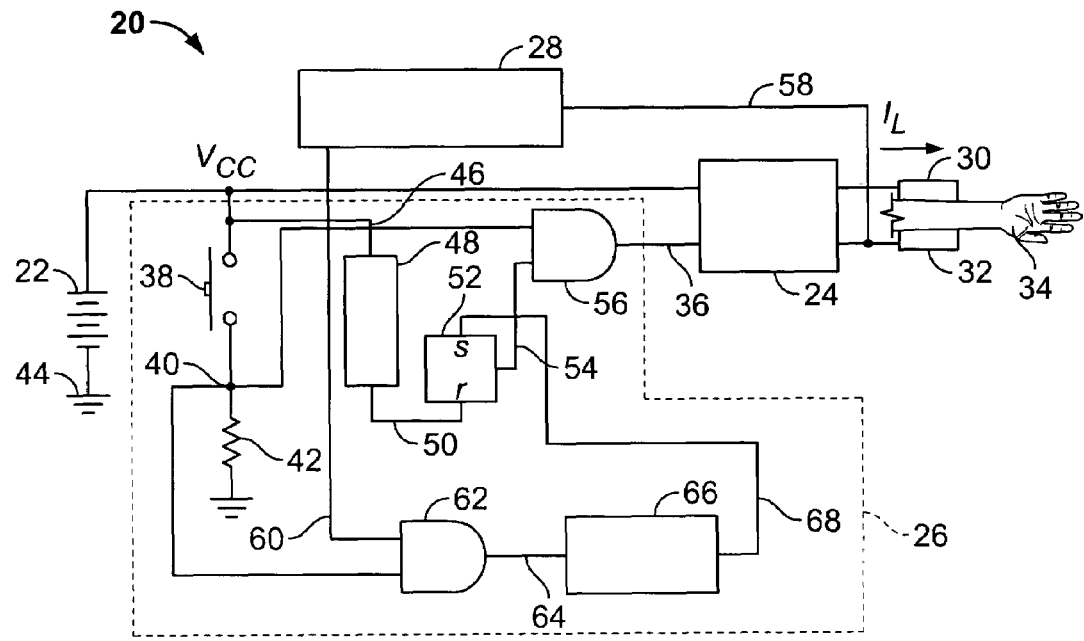
FIG. 1 is a schematic diagram of an electrotransport device having a timer controlling a permanent disabling means in accordance with this invention.

Referring now to FIG. 1, there is shown one embodiment of an electrotransport delivery device generally indicated by numeral 20. The device 20 includes a power source 22, a current generating and controlling circuit 24, and an enabling/disabling circuit 26. The circuit 26 includes a permanent, irreversibly disabling function in accordance with this invention. The device 20 also includes current output electrodes 30, 32 for contacting the patient's body surface (eg, skin) 34. The electrodes 30, 32 are connected to the current controlling circuit 24. The device 20 may optionally include a load current sensing circuit 28.

The power source 22 (indicated as a battery) provides a DC supply voltage Vcc. The current generating and controlling circuit 24, the enabling/disabling circuit 26 and the sensing circuit 28 obtain power from one terminal of the power source 22 indicated as Vcc and return connections (not shown) to a ground 44 of device 20.

The electrodes 30, 32 may be configured to contain one or more therapeutic agents in liquid, gel or other suitable form. At least one of electrodes 30, 32 contains the therapeutic agent to be delivered. The electrodes 30, 32 may be held in place on the patient by adhesive overlays or any of the conventional methods used to secure passive transdermal delivery devices to the skin.

The electrotransport delivery device of the present invention is preferably flexible enough to conform to contours of the body. While not limited to any particular size or shape, the device illustrated in FIG. 1 is typically about 5 to 10 cm long, about 2 to 5 cm wide, and has a thickness of approximately 0.5 to 3 cm. The combined skin-contacting areas of electrodes 30, 32 can vary from less than 1 cm$^2$ to greater than 200 cm$^2$. The average device however, will have electrodes with a combined skin-contacting area within the range of about 5 to 50 cm$^2$. As constructed the device 20 with electrodes 30, 32 form an open circuit until such time as when the electrodes 30, 32 are applied to the human body, whereupon a circuit through the human tissue is completed between the electrodes 30, 32.

Enabling Delivery of the Agent

The current controlling circuit 24 has current output electrodes 30, 32. The electrodes 30, 32 are configured to provide electrically assisted delivery of one or more therapeutic agents through a subject's skin 34 when load current $I_L$ flows through the electrodes 30, 32 and the skin 34. The circuit 24 also has a control input 36 for enabling and disabling the output current $I_L$ through electrodes 30, 32. The circuit 24 is configured such that no load current $I_L$, will be output as long as signal 36 remains low. The circuit 24 is configured to generate one or more types of current flow, $I_L$, such as DC, AC, pulsed DC, pulsed AC, or any suitable combinations of waveforms as dictated by the requirements of the treatment at hand when the signal 36 goes high. Enabling of a high level on the signal 36 is described below.

Enabling/Disabling Circuit

In one embodiment of the present invention, the enabling/disabling circuit 26 includes a user activation switch 38 connected from Vcc to one terminal 40 of a resistor 42. The other terminal of the resistor 42 is connected to the system ground 44.

A power on reset circuit (POR) 48 has an input signal 46 and an output signal 50. The POR circuit 48 is activated by the positive going signal 46 when POR circuit 48 is connected to the power source 22. This occurs, typically, when the device 20 is manufactured. The POR circuit 48 causes a high level on the signal 50 after a short delay time. The signal 50 activates reset r on a Flip Flop (FF) 52 when the signal 50 goes high. The reset r of the FF 52 causes the complementary output signal 54 of FF 52 to go high. A high level on the signal 54 enables one input of a 2-input AND gate 56.

The terminal 40 of the resistor 42 is connected to the other input of the AND gate 56. Closure of switch 38 causes a high level on signal 40. The combination of high levels on the signal 40 and the signal 54 causes the AND gate 56 to output a high level on signal 36. A high level on signal 36 enables the current generating and controlling circuit 24 to provide the appropriate current waveform $I_L$ through electrodes 30, 32 for delivery of the therapeutic agent when the electrodes 30, 32 are suitably in contact with the skin 34.

Delivery of the therapeutic agent from at least one of the electrodes 30, 32 through the skin 34 will continue until the electrodes 30, 32 are removed from the skin 34, or the current generating and controlling circuit 24 is disabled.

The current generating and controlling circuit 24 may also include a preset timer (not shown) for delivering the predetermined current waveform $I_L$ for a predetermined time $T_{del}$ after initiating the switch 38 whereby a predetermined dose of the therapeutic agent is automatically delivered over time period $T_{del}$ every time switch 38 is closed. This provides a patient having the device 20 applied, with an opportunity to deliver a pain relieving agent as needed. This avoids the necessity of having an attendant, such as a nurse, present to obtain and deliver the agent. It also avoids the necessity of having the patient attached to an intravenous (IV) or subcutaneous (SC) infusion delivery system with the associated costs and risks of setting and maintaining the proper dosage level and safe and effective connections.

Individuals have widely varying tolerance to pain. In addition, patients who receive narcotic analgesics tend to quickly develop a tolerance whereby larger and lager doses are required to control pain. Device 20 allows each patient to individually control the amount of drug (eg, narcotic analgesic) delivered in order to effectively control pain as perceived by the patient. The automatic and permanent disabling feature in accordance with this invention, provides the necessary element of safety and control to limit potential abuse.

Permanent Disabling of the Delivery of the Agent

The output signal 60 connects to one of the inputs of a second 2-input AND gate 62. The other input of the gate 62 is connected to the resistor terminal 40. The AND gate 62 has an output 64 which goes high when both signal 60 and the signal 40 are high. The output 64 enables a timer 66 which is configured to output a high level on the signal 68 after some predetermined period of time, Tmax, after the signal 64 goes high.

The signal 68 is connected to a set input s of the FF 52. The FF 52 will output a low level on the signal 54 when the s input goes high. The low level on the signal 54 causes the AND gate 56 to output a low level on the signal 36 which disables the current generating circuit 24 from supplying further current $I_l$ to the electrodes 30, 32 and the skin 34. The FF 52 remains in the state caused by the last occurrence of a high level on either the reset input signal 50 or the set input signal 68. Since the output 50 of POR circuit 48 can no longer change, the set input signal 68 was the last to change and the FF 54 is in a permanent set state with signal 54 low. The current generating and controlling circuit 24 is therefore permanently and irreversibly disabled from supplying load current $I_L$ through electrodes 30, 32.

The electrically assisted delivery of the therapeutic agent will therefore be permanently stopped at the expiration of the time Tmax by the timer 66.

Protection from Inadvertent Permanent Disabling

In the event that the electrodes 30, 32 are not in good contact with the skin 34, it is an advantage to protect against the activation of the permanent disabling function of this invention to prevent unwanted disabling of the electrotransport device 20. This may occur, for example, by inadvertently pressing the switch 38 before the device is positioned on the skin 34, eg, while the device is being packaged, shipped or removed from its package. The current sensing circuit 28 is provided to postpone the application of the disabling function. One implementation of this is described with further reference to FIG. 1.

A current sensing signal 58 is coupled to one of the electrodes 30, 32. The current sensing signal 58 activates the current sensing circuit 28 when the load current $I_L$ exceeds some preselected minimum Imin, say, 25 uA. The load current $I_L$ in operation is designed to be a predetermined value Io, typically on the order of 1 mA. The current sensing circuit 58 has an output signal 60 which goes high when the electrodes 30, 32 are in proper position on the skin 34, and the current generating and controlling circuit 24 is enabled by the enabling output 36 of AND gate 56.

If the switch 38 is inadvertently closed before the proper electrode 30, 32 and skin 34 contact is made, $I_L$ will not reach the preselected minimum, Imin. The current sensing circuit 28 output 60 will be low thereby causing the output 64 of AND gate 62 to remain low, with the result that, the timing circuit 66 will not be activated. The current generating and controlling circuit 24 can still thereafter be enabled by depressing switch 38 since delivery of current $I_L$ from circuit 24 depends only on the contact of the electrodes 30, 32 and the skin 34.

When proper contact is made and the current $I_L$ increases above the minimum level Imin, the sensing circuit 28 enables the AND gate 62 and the current generating and controlling circuit 24 as described above.

The beginning of the effective delivery of the therapeutic agent is determined to be when both the demand for the agent, as represented by the closure of switch 38, and the effective skin contact, as represented by a load current $I_L$ above the predetermined current limit, Imin, are satisfied.

Permanent Disabling by Dose Count

Figure 2:
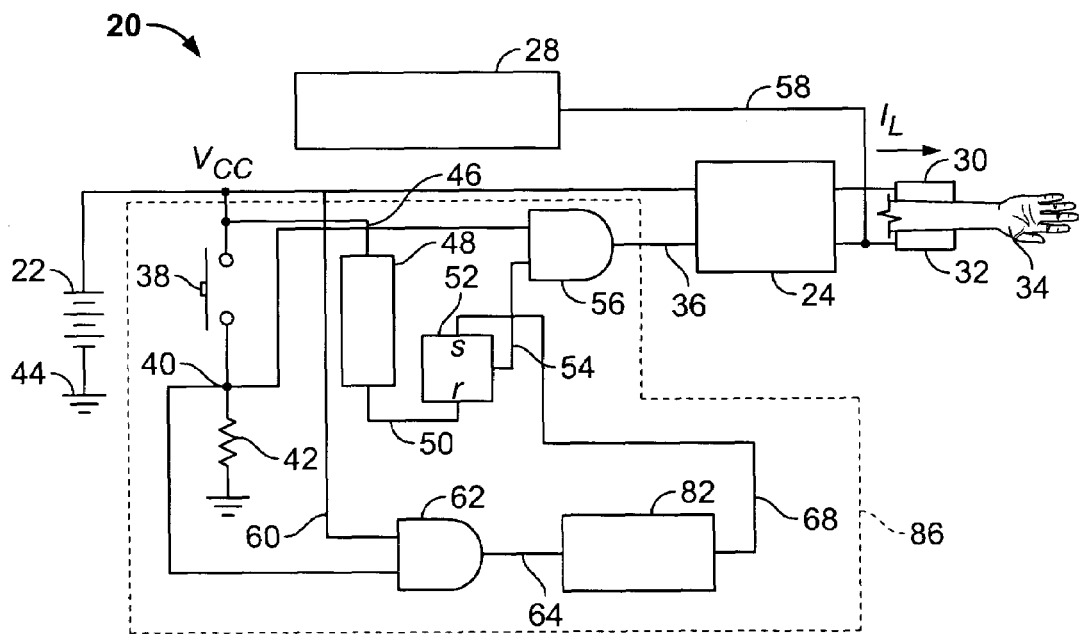
FIG. 2 is a schematic diagram of an electrotransport device having a counter controlling a permanent disabling means in accordance with this invention.

With reference to FIG. 2, another embodiment of the permanent delivery disabling feature of the present invention is shown. An electrotransport device 80 includes a power source 22, a current generating and controlling circuit 24, as before described and an alternative enabling/disabling circuit 86. The circuit 86 includes a POR circuit 48, a switch 38, a resistor 42, a FF 52, an AND gate 62 and an AND gate 56 as before. The circuit 86 also includes a dose counter circuit 82 to provide a permanent, irreversibly disabling function in accordance with this invention. The device 80 may also include a load current sensing circuit 28.

For each initiation of the switch 38 causing current $I_L$ to flow following application of the electrodes 30, 32 to the skin 34, the current generating and controlling circuit 24 will deliver the predetermined level and duration of current. Each successive closure of switch 38 will cause a high level on the signal 40. As long as the sensing circuit 28 senses the current $I_L$ to be above the minimum Imin, the signal 60 will be high. The sensing circuit 28 output signal 60 connects to one of the inputs of the second 2-input AND gate 62. The other input of the AND gate 62 is connected to the resistor terminal 40. The AND gate 62 output 64 makes a transition from low to high when the last of signal 60 and the signal 40 transitions from low to high.

A low to high transition on the output 64 enables a dose counter circuit 82 to increment one count at the beginning of each dose delivery. The dose counter circuit 82 is configured to increment one count for each dose delivered. The counter circuit 82 is configured to output a high level on the signal 68 at some predetermined dose count number, Nb, of doses delivered by the device 80 after the signal 64 goes high.

The signal 68 is connected to a set input s of the FF 52. The FF 52 will output a low level on the signal 54 when the s input goes high. The low level on the signal 54 causes the AND gate 56 to output a low level on the signal 36 which disables the current generating circuit 24 from supplying further current $I_L$ to the electrodes 30, 32 and the skin 34. The delivery of the subject therapeutic agent will be therefore be stopped when the counter circuit 82 reaches the predetermined dose count Nb. The FF 52 remains in the state caused by the last occurrence of a high level on either the reset input signal 50 or the set input signal 68. Since the output 50 of the POR circuit 48 can no longer change, the set input signal 68 was the last to change and the FF 54 is in a permanent set state with the signal 54 low. The current generating circuit 24 is therefore permanently and irreversibly disabled from supplying load current $I_L$.

Permanent Disabling to Prevent Use of Device Beyond Acceptable Shelf-Life

Figure 3:
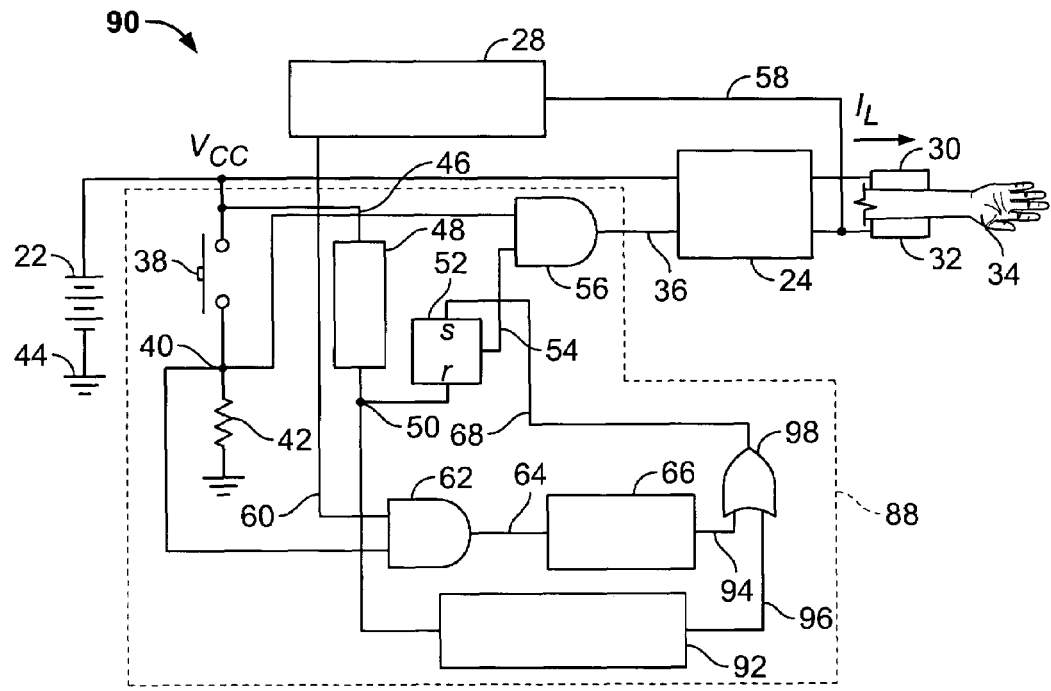
FIG. 3 is a schematic diagram of an electrotransport device having a timer for permanently disabling the device after a predetermined period after manufacture of the device.

With reference to FIG. 3, yet another embodiment of an electrotransport device 90 having a permanent disabling capability in accordance with the present invention is shown. Device 90 has an enabling/disabling circuit 88 which incorporates the "timer" disabling circuit 66 of FIG. 1 and in addition a second long-range timer 92 and an OR gate 98. To guard against undesired use of the device 90 after the device (or portions thereof, such as the power source/battery 22) or the therapeutic agent contained in one of electrodes 30, 32 has exceeded a useful shelf life, the device 90 includes the second timer 92 for permanently disabling the device 90 in addition to the first timer 66 of FIG. 1. The second timer 92 is configured to output a high level on an output signal 96 at a predetermined time, T2max, such as 2 years, after the timer 92 is activated.

Connection and operation of the POR circuit 48, the sensing circuit 28, the switch 38, the current generating circuit 24, the FF 52 and the AND gates 56 and 62 are as described before with regard to FIG. 1. The input of the timer 92 is connected to the output 50 of POR circuit 48. The timer 92 has the output 96 connected to one input of the OR gate 98. The timer 66 has an output 94 connected to the other input of the OR gate 98. The OR gate 98 provides an output signal 68 to the set input s of the FF 52. The occurrence of a high level on either signal 94 or 96 will cause the output 68 to go high. A high level on signal 68 will reset the FF 52, thereby disabling the current generating circuit 24, as before described.

When the device 90 is manufactured, the battery 22 is installed, thereby causing a high level on the signal 46 initiating the POR circuit 48. The POR circuit 48 will output a high level on the signal 50 after a short delay. The timer 92 will be activated by the high level on the signal 50 and start counting. The timer 92 will output a high level on the signal 96 at the end of the predetermined period from manufacture, T2max. Since the OR gate 98 will output a high level on the signal 68 on the occurrence of a high level on either the inputs 94 or 96, the device 90 will be permanently and irreversibly disabled by the elapse of the 24 hour time limit of the timer 66 from first use of the device 90, or by the elapse of the 2 year time limit from when the timer circuit 91 is manufactured, whichever comes first.

Disablement by Battery Discharge

Figure 4:
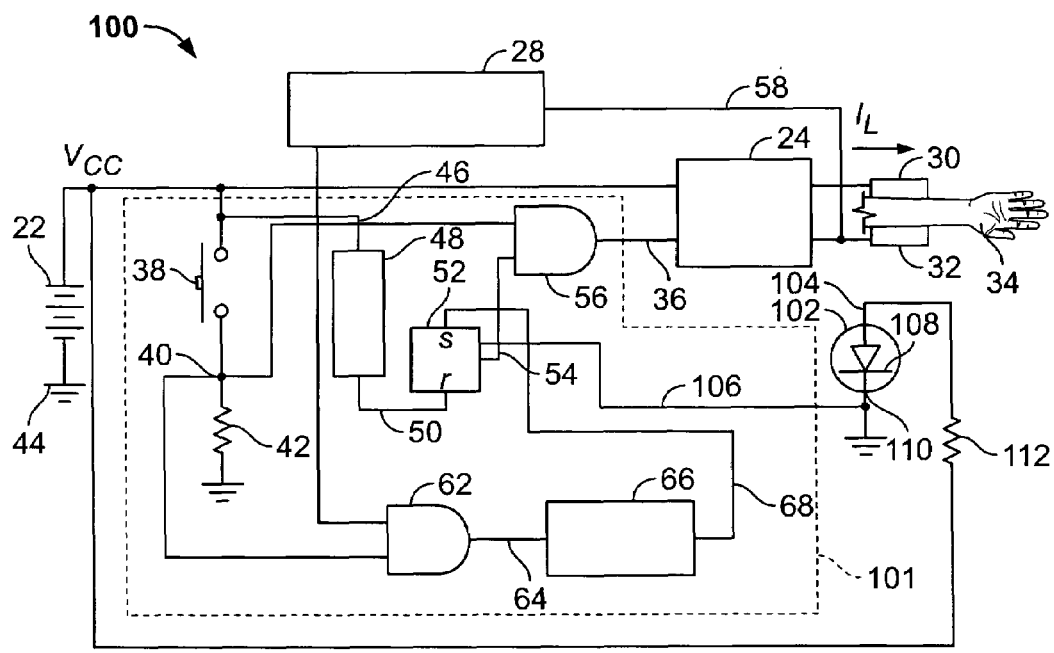
FIG. 4 is a schematic diagram of an electrotransport device having a silicon controlled rectifier (SCR) for rapidly discharging a battery power source to permanently disable the device.

An embodiment of an electrotransport delivery device 100 having an alternate permanent current disabling circuit 101 is shown in FIG. 4. Connection and operation of the POR circuit 48, the sensing circuit 28, the switch 38, the current generating circuit 24, the FF 52 and the AND gates 56 and 62 are as described before with regard to FIG. 1. The FF 52 also includes an output 106 which goes high when FF 52 is set. The device 100 includes a silicon controlled rectifier (SCR) 102 for rapidly and permanently discharging the battery 22. The SCR 102 has a collector 104 connected to the positive terminal of the battery 22 through a limiting resistor 112. The SCR 102 has a gate 108 connected to the output 106, and a cathode 110 connected to ground 44.

In operation, as described above, the timer 66 will time out at the end of the predetermined period (eg, 24 hours), and provide a high level to the set input 68 of the FF 52. The FF 52 will output a high level on signal 106 which will fire the SCR 102. The value of the resistor 112 is selected to provide a rapid, but safe discharge of the battery 22. Complete discharge of the battery 22 will permanently and irreversibly disable current flow to the electrodes 30, 32.

Disablement by Delivery Current Shunting

Figure 5:
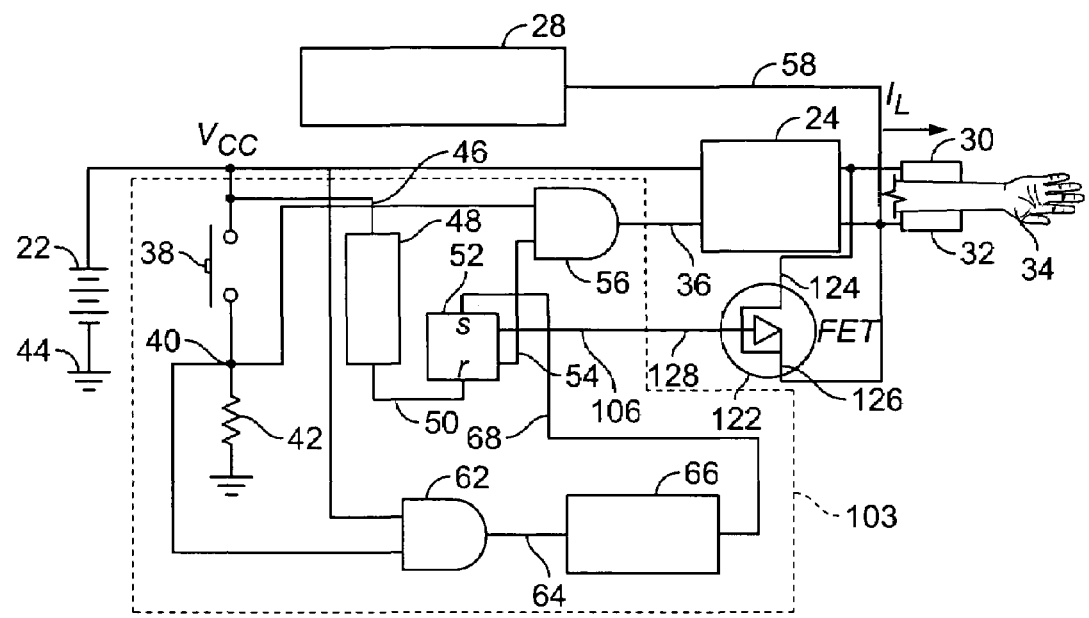
FIG. 5 is a schematic diagram of an electrotransport device having a field effect transistor (FET) for shunting the delivery current from the delivery electrodes to permanently disable the device.

An electrotransport delivery device 120 having an alternate permanent current disabling circuit 103 is shown in FIG. 5. Connection and operation of the POR circuit 48, the sensing circuit 28, the switch 38, the current generating circuit 24, the FF 52 and the AND gates 56 and 62 are as described before with regard to FIG. 1. The FF 52 also includes an output 106 which goes high when FF 52 is set. The device 120 includes a field effect transistor (FET) 122. The FET 122 has a drain 124 connected to one electrode 30, and a source 126 connected to the other electrode 32. The FET 122 has a gate 128 connected to the output 106.

In operation, as described above, The timer 66 will time out at the end of the predetermined period (eg, 24 hours), and provide a high level to the set input 68 of the FF 52. The FF 52 will output a high level on signal 106 which will turn on the FET 122 and place a low resistance path from drain 124 to source 126 in parallel with the electrodes 30, 32. The low resistance path will divert the load current $I_L$ from the electrodes 30, 32 thereby permanently and irreversibly disabling the electrically assisted delivery of the therapeutic agent contained in the at least one of the electrodes 30, 32.

Disablement from Body Parameter Limit Sensing and Comparison

Figure 6:
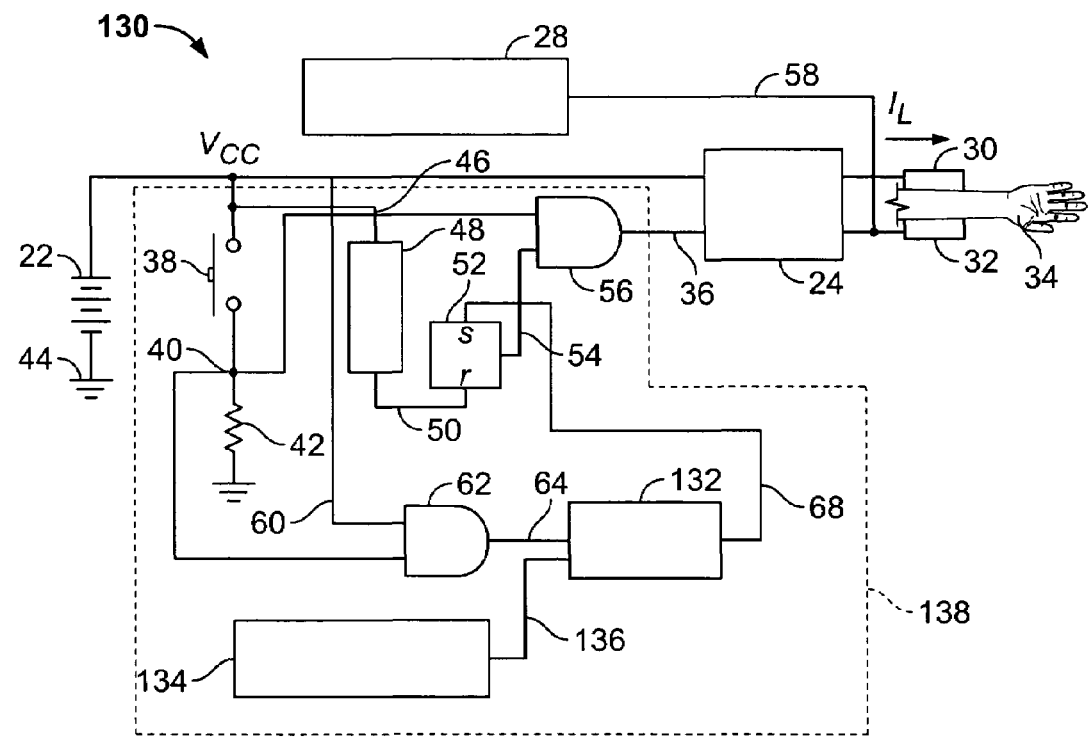
FIG. 6 is a schematic diagram of an electrotransport device having a body parameter sense and compare circuit for permanently disabling the device when a body parameter exceeds some predetermined limit.

An electrotransport delivery device 130 having an alternate permanent current disabling circuit 138 is shown in FIG. 6. Connection and operation of the POR circuit 48, the sensing circuit 28, the switch 38, the current generating circuit 24, the FF 52 and the AND gates 56 and 62 are as described before with regard to FIG. 1 and the operation of the device 20.

The device 130 includes a body parameter sensor 134 for detecting a body parameter such as heart rate, body temperature, sweating, breathing rate, blood or tissue oxygen content, blood or tissue carbon dioxide content, blood pressure, blood glucose content, composition of sweat, motion (movement), and a sense/compare circuit 132 which compares the sensed body parameter to some predetermined limit, Lp. The sensor 134 may be an "on-board" component of the delivery device 130 or may be a separate self-contained unit remote from the delivery device 130 but connected into circuit 132 using standard electrical connectors (eg, cables). One input of the sense/compare circuit 132 is connected to the output 64 of the AND gate 62. Another input of the sense/compare circuit 132 is connected to the parameter sensor 134 by signal 136. The sense/compare circuit 132 is configured to output a high level on signal 68 when the output 64 is high and the body parameter as measured by the sensor 134 exceeds the predetermined limit Lp.

As described above with reference to the operation of device 20, the signal 68 is connected to a set input s of the FF 52. The FF 52 will output a low level on the signal 54 when the s input goes high. The low level on the signal 54 causes the AND gate 56 to output a low level on the signal 36 which disables the current generating circuit 24 from supplying further current $I_L$ to the electrodes 30, 32 and the skin 34. The FF 52 remains in the state caused by the last occurrence of a high level on either the reset input signal 50 or the set input signal 68. Since the output 50 of POR circuit 48 can no longer change after the battery 22 is connected (ie, at the time device 130 is manufactured), the set input signal 68 is the last to change and the FF 52 is in a permanent set state with the signal 54 low. The current generating circuit 24 is therefore permanently and irreversibly disabled from supplying load current $I_L$ to the electrodes 30, 32.

Figure 7:
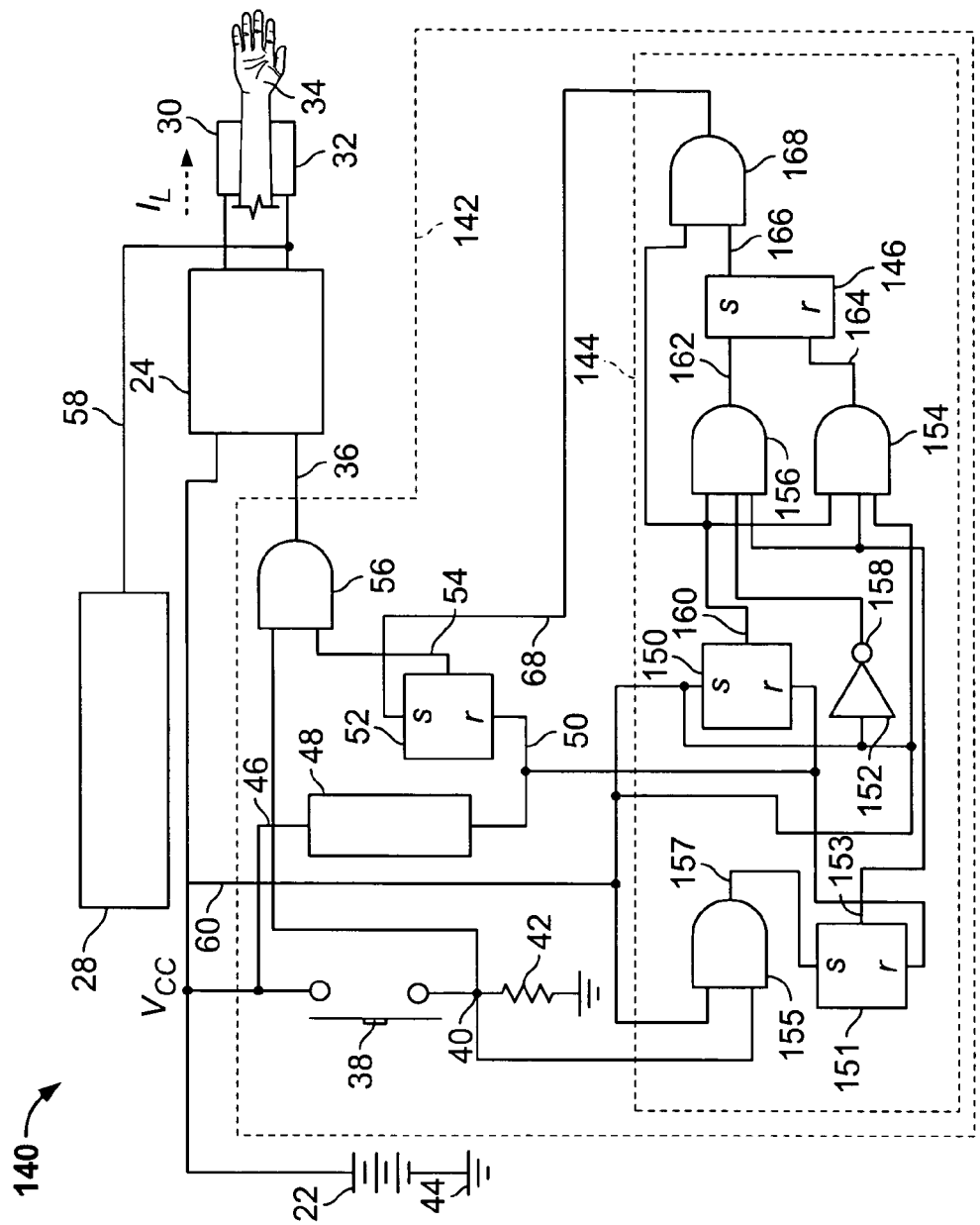
FIG. 7. is a schematic diagram of an electrotransport device having a circuit for permanently disabling the device when the delivery current has been interrupted for a predetermined period of time after initiation of delivery.

Prevention of Permanent Disabling after Inadvertent and Brief Removal of the Electrodes With regard to FIG. 7, there is shown an electrotransport device 140 having an enabling/disabling circuit 142 including a time-from-removal circuit 144. The circuit 142 has a number of similar components found in circuit 26 shown in FIG. 1, including a user activation switch 38, a resistor 42, a POR circuit 48, the power source 22, a FF 52, the AND gate 56 and the current generating circuit 24 which supplies a drive current $I_L$ to electrodes 30, 32.

The time-from-removal circuit 144 includes two edge triggered set-reset Flip-Flops (FF) 150 and 151, an inverter 152, two three-input AND gates 154 and 156, two-input AND gates 155 and 168 and a set-reset timer circuit 146.

The POR circuit output 50 is connected to the reset inputs of the FF's 150 and 151. The output 60 of the circuit 28 is connected to one of the inputs of the two-input AND gate 155, the set input of the FF 150, the input of the inverter 152 and to the first input of the AND gate 154. The output 157 of AND gate 155 is connected to the set input of the FF 151. The output 153 of the FF 151 is connected to the second of the three inputs of AND gates 154 and 156. The output 160 of the FF 150 is connected to the third input of the AND gates 154 and 156, and to the first input of the AND gate 168. The output 158 of the inverter 152 is connected to the first input of the AND gate 156.

The output 162 of the AND gate 156 is connected to the edge triggered set input of the timer circuit 146. The output 164 of the AND gate 154 is connected to the edge triggered reset input of the timer circuit 146. The output 166 of the timer circuit 146 is connected to the second input of the AND gate 168. The output of the timer circuit 146 is connected to the edge triggered set input of the FF 52. The other connections for the switch 38, the resistor 42, the POR circuit 48, the FF 52, the AND gate 56, the current generating circuit 24 and sense circuit 28 are as heretofore described.

Delivery of the therapeutic agent will be initiated as described above by action of the switch 38, the POR circuit 48 and the FF 52 after application of the electrodes 30, 32 to the skin 34. Delivery from the electrodes 30, 32 through the skin 34 will continue until at least one of the electrodes 30, 32 are removed from the skin 34, or the current generating circuit 24 is disabled. If a brief removal of the electrodes 30, 32 occurs (eg, device 140 is dislodged from the patient's skin 34 while removing clothing), the device 140 may be quickly reapplied to the skin without initiating the automatic disabling circuit.

This is accomplished in the following manner. The sensing circuit 28 is configured to transition to a high level on the signal 60 when the current $I_L$ reaches a desired predetermined level and to transition to a low level when the current $I_L$ drops to zero when one or both of the electrodes 30, 32 are removed from the skin 34.

However, current will not flow until after the electrodes 30, 32 are place in contact with the skin 34 and the switch 38 is activated. When switch 38 is activated, it will cause a high level on signal 40. Since the signal 54 is already high from the reset of FF 52 by POR circuit 48, the AND gate 56 will output a high level on signal 36 to the current generating circuit 24. If the electrodes 30, 32 are in place, current will begin to flow and the sense circuit 28 will output a positive transition on signal 60.

The transition to a high level on signal 60 causes the edge triggered FF 150 to transition to a high level on the output 160. The inverter 152 causes a transition to a low level on the output 158.

The high level on the signal 40 in combination with the high level on the signal 60 will enable the AND gate 157 to output a positive transition on the signal 157. The positive transition of signal 157 causes the edge triggered FF 151 to output a high level on the signal 153. The high level on signal 153 and on signal 160 enable both the AND gates 154 and 156 whose output logic states will depend only on the complementary signals 152 and 158.

At this state, the circuit 140 is delivering current $I_L$ to the electrodes 30,32 through the skin 34. If the current delivery is interrupted, the sense signal 58 will go low, causing a low level on the output 60 of the sense circuit 28. The low going transition on signal 60 will cause the inverter 152 to output a positive going transition on signal 158. A positive going transition on signal 158 will cause a positive going transition of the output 156 of AND gate 156. A positive transition on the edge triggered set input of the timer 146 will start the timer counting to a predetermined value, Tr. If the current remains interrupted for a period exceeding the predetermined value, Tr, the timer 146 will output a high level on the signal 166. Since the signal 160 is already high, both of the inputs of the two-input AND gate 168 will be high. The AND gate 168 will cause the signal 68 to go high, thereby causing the edge triggered set input of FF 52 to reset the output signal 54 low. A low level on signal 54 will cause the current generating circuit 24 to be disabled, so that load current $I_L$ will not flow even if the electrodes 30, 32 are reconnected. This will result in permanent and irreversible disabling of the electrotransport device 140.

If the electrodes 30, 32 are reconnected to the skin 34 before the timer 146 reaches the predetermined limit, the circuit 24 will still be enabled and load current $I_L$ will flow once more. The sense circuit 28 will thus output a positive transition on signal 60. The positive transition of signal 60 will cause the output 164 of the AND gate 154 to make a positive transition on the edge triggered reset input of the timer circuit 146. The reset of the timer 146 will prevent an output transition on signal 166. The load current will thus continue to flow until disabled by some other means.

Permanent Disabling after Predetermined Amount of Current Applied

Figure 8:
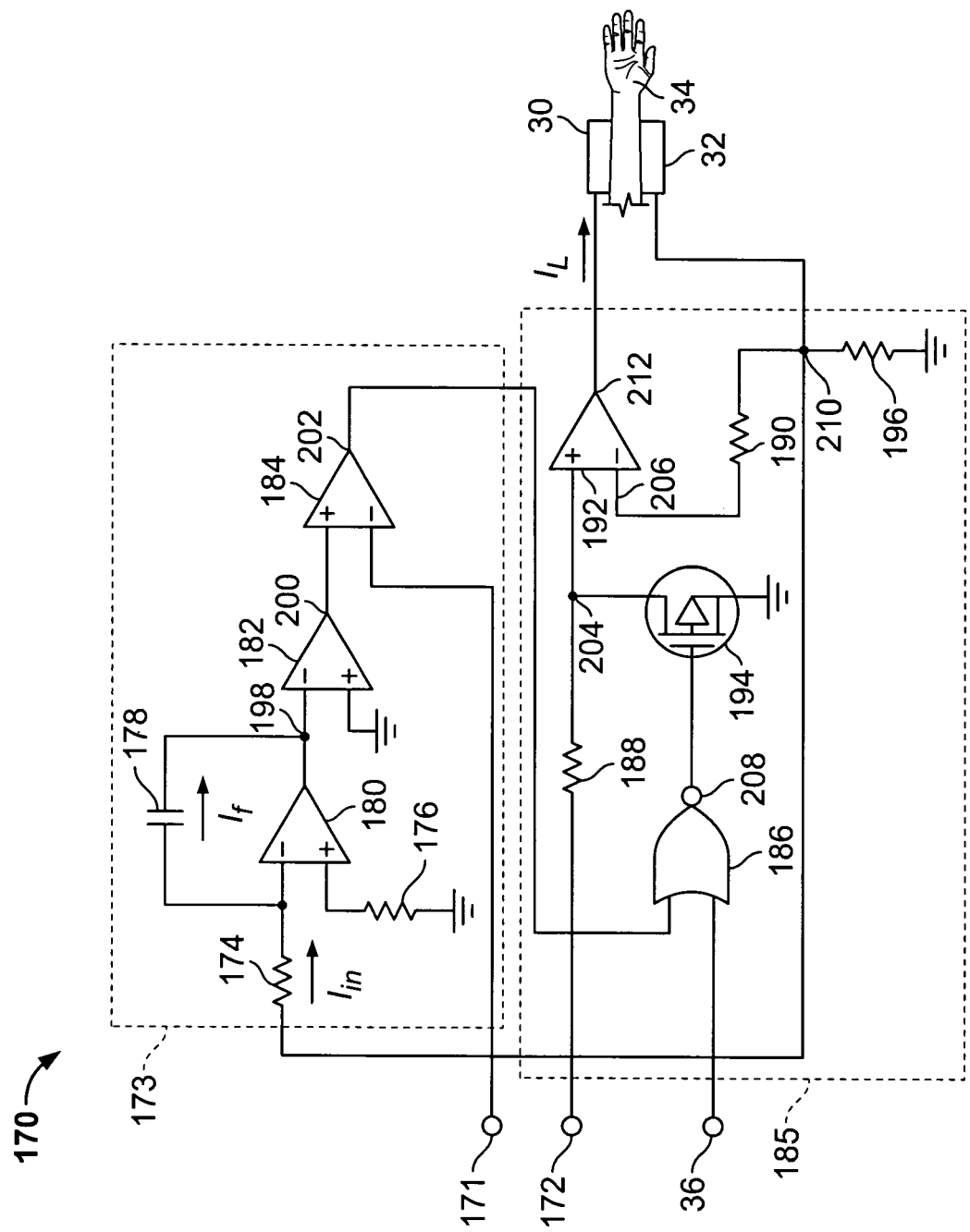
FIG. 8. is a schematic diagram of a current integrating limiting circuit for permanently disabling an electrotransport device after a predetermined amount of electric current has been applied by the device.

With reference to FIGS. 7 and 8, another embodiment of a permanent disabling electrotransport device is shown. FIG. 8 depicts the detail of a current control and total current limiting circuit generally indicated by numeral 170, which may be incorporated within the circuit illustrated in FIG. 7. The circuit 170 is shown as the combination of a current integrating circuit 173 and a current generating and logic disabling circuit 185. The circuit 173 is configured to integrate the total current $I_L$ supplied by the generating circuit 24 of FIG. 7, through the electrodes 30, 32 and the skin 34 and supply a signal to disable the current generating circuit when the cumulative current delivered reaches some predetermined value, $Q_t$.

The circuit 170 includes three high gain, high input impedance, differential amplifiers 180, 182 and 184 wherein each amplifier includes an output node 198, 200, 202 respectively. Each amplifier 180, 182 and 184 includes an inverting and non-inverting input. The circuit 170 also includes two input resistors 174, 176 and a feed back capacitor 178. One terminal of the resistor 174 is connected to a feedback signal 210 which is proportional to the load current $I_L$. The other terminal of the resistor 174 connects to the inverting input of the amplifier 180.

One side of the feedback capacitor 178 is connected to the output 198 of the amplifier 180. The other side of the capacitor 178 is connected to the inverting input of the amplifier 180. A second input resistor 176 is connected between the non-inverting input of the amplifier 180 and ground 44.

The output of the amplifier 180 is also connected to the inverting input of the amplifier 182. The non-inverting input of the amplifier 182 is connected to ground 44. The output 200 of the amplifier 182 is connected to the non-inverting input of the amplifier 184. The inverting input of the amplifier 184 is connected to a reference voltage 171 which is supplied by a reference voltage source such as voltage divider (not shown). The reference voltage 171 establishes the maximum value of the integral of the load current $I_L$, denoted by $Q_L$, which is to be supplied to the electrodes 30 and 32.

The current generating and disablement logic circuit 185 includes a high gain differential amplifier 192 having an non-inverting input 204, in inverting input 206 and an output 212. The circuit 185 also includes an input resistor 188, a feed back resistor 190, a two input OR 186 gate having an output 208, an FET 194, and a sense resistor 196. One terminal of the input resistor 188 is connected to a reference voltage 172 from a reference voltage source (not shown) such as a voltage divider. The voltage 172 establishes the predetermined value of current $I_L$ to be delivered to the skin 34 by the electrodes 30 and 32. The other terminal of the resistor 188 is connected to the non-inverting input of the amplifier 192. One terminal of the feed back resistor 190 is connected to the inverting input of the amplifier 192. The other terminal of the resistor 190 is connected to the sense terminal 210 of the sense resistor 196.

One input of the two input OR gate 186 is connected to the output 202 of the amplifier 184. The other input of the OR gate 186 is connected to a disabling signal 36 shown in FIG. 7. The output 208 of the OR gate is connected to the input gate of the FET 194. The drain 204 of the FET 194 is connected to the non-inverting input of the amplifier 192. The output 212 of the amplifier 192 connects to the electrode 30. The return electrode 32 connects to the common sense point 210 of the resistors 190 and 196.

The values of the input resistors 174, 176, 188, and 190 are typically several orders of magnitude greater than the sense resistor 196. Whereas the value of the sense resistor 196 may be chosen to be 10 ohms, the value of the input resistors 174, 176, 188, and 190 may be 100 k ohms. Therefore, substantially all the load current, $I_L$, will flow through the sense resistor 196, with the result that the voltage on signal 210 will be proportional to the load current, $I_L$.

The voltage gain of the amplifiers 180, 182, 184, and 192 are selected to be several thousand, so that very small input signals will be greatly amplified. The amplifiers 180, 182, 184, and 192 are selected to have sufficiently low input noise and input leakage to give accurate operation. The amplifiers 180, 182, 184 and 192 are selected to have sufficiently high input impedance to present negligible loading on the other circuit elements. The selection of suitable components is within the capability of those skilled in the art of amplifier design.

In operation, the electrodes 30 and 32 are attached to the skin 34. Initially, current flow is zero. The sense signal 210 is therefore also zero. Current flow $I_L$ is initiated by the person controlling the electrotransport device 140. The voltage reference on signal 172 is established by the voltage divider (not shown). The initial state of the inputs 36 and 202 to the OR gate 186 are both low, so the output 208 is also low. The gate of the FET 194 being low, causes the drain of the FET 194 to present an essentially open circuit to the signal 204. The high impedance of the non-inverting input of amplifier 192 causes essentially all of the voltage at signal 172 to appear on the signal 204. The high gain of the amplifier 192 causes the output signal 212 to rise to a value sufficient to increase the load current $I_L$ to a value such that $I_L$ times the resistance of the sense resistor 196 will produce an essentially equal voltage at the non-inverting input 206 of the amplifier 192. The current $I_L$ will therefore track the value of the reference voltage on signal 172.

The signal voltage 210 will be transferred by the input resistor 174 to the inverting input of the amplifier 180. Since the non-inverting input of amplifier 180 is at ground, the inverting input of amplifier 180 will also be constrained to be near ground. This is accomplished by causing a feedback current $I_f$ in the feedback capacitor 178 which exactly balances the input current $I_{in}$. The required current $I_f$ is achieved by the voltage on the output 198 appearing as an inverted integral of the sense voltage on signal 210. For example, if the input reference voltage on signal 176 is a positive constant value, the output voltage on signal 198 will be a negative going ramp. The current $I_f$ flowing in capacitor to exactly balance the input current $I_{in}$.

The inverting amplifier 182 is an amplifier having a gain of −1, such that a positive value proportional to the integral of the load current $I_L$ appears at the non-inverting input of the amplifier 202. The amplifier 202 is operated as a high gain threshold detector, with the reference switching value provided by the reference voltage on signal 171. The signal 171 comes from a voltage divider (not shown). The value of the signal 171 is selected to represent the desired total dose, $Q_r$. When the value of the signal 200 becomes more positive than the reference value on signal 171, the output 202 of the amplifier 184 switches rapidly from zero to the maximum supply voltage Vcc. A positive voltage on signal 202 causes the output 208 of OR gate 186 to go positive, driving the drain 204 of the FET 194 into a high conducting state. The drain 204 of the FET 194 thereby grounds the non-inverting input of the amplifier 192. The output 212 of the amplifier 192 is thus driven to ground, causing cessation of load current $I_L$. Since the circuit 170 remains active as long as power is supplied by the battery 22, the load current $I_L$ is permanently and irreversibly disabled.

Mechanical Disablement of Electrotransport Current

Figure 9:
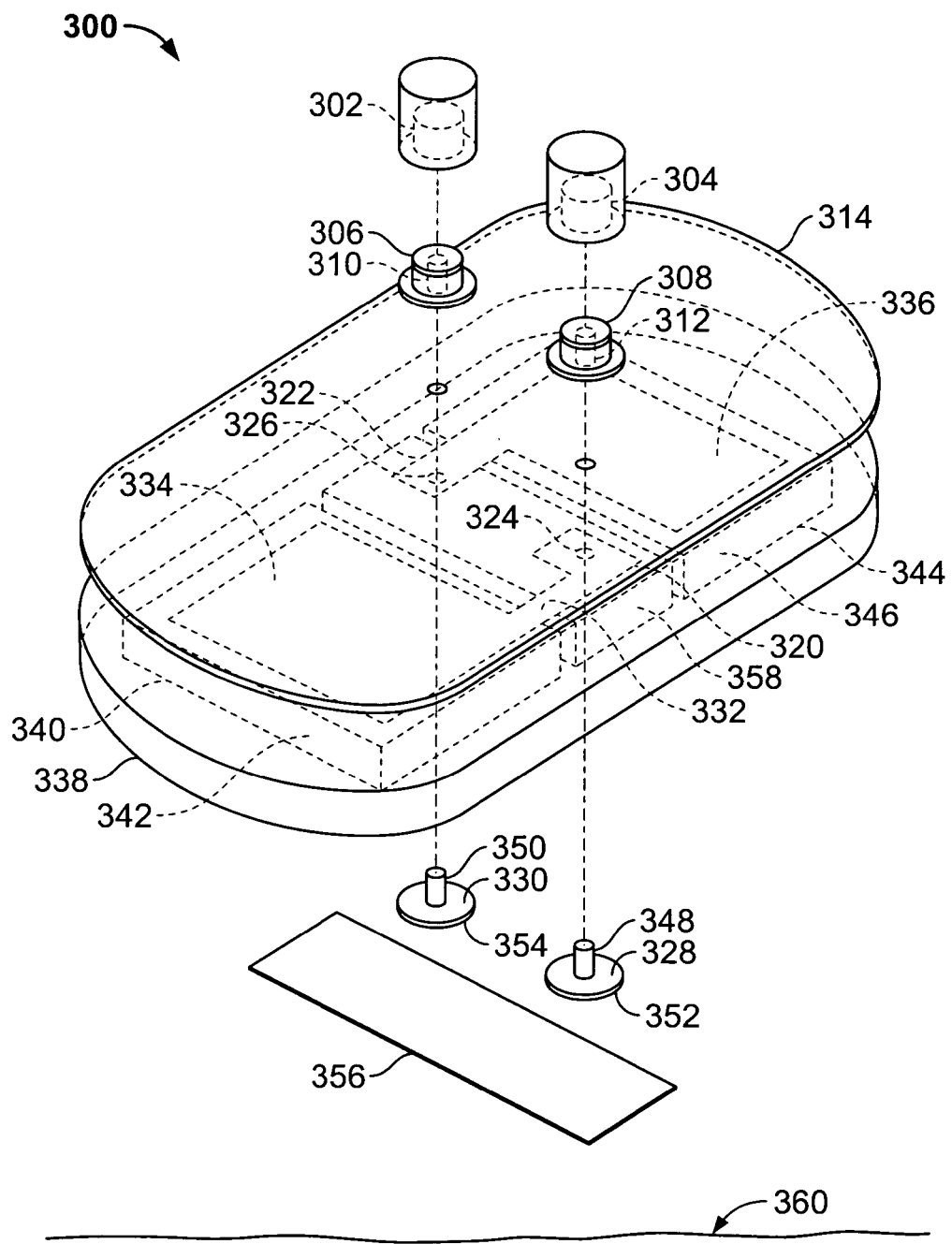
FIG. 9 is an exploded perspective view of a disposable/single use electrode assembly having a electrical connection circuit including a frangible conducting member.

The permanent disablement of electrotransport current for a electrotransport device may also be achieved by non-electronic means according to another aspect of the present invention. This means for permanent disablement is particularly well suited for electrotransport devices having a reusable component, which typically contains electrical circuitry and other hardware suited for longer term use, and a single use/disposable component, which typically contains the drug (donor) and electrolyte salt (counter) reservoirs and optionally the electric power source (eg, a battery). Examples of such two-part electrotransport devices are disclosed in Newman U.S. Pat. No. 4,942,883; Bock et al U.S. Pat. No. 5,037,381; Sibalis et al U.S. Pat. Nos. 4,731,926; 5,135,479 and 5,167,617; and Devane et al published UK patent application 2,239,803A, all of which are incorporated herein by reference. In these 2-part electrotransport devices, it is most desirable to permanently disable only the drug-containing single/use disposable portion so that the reusable portion, which contains the electrical circuitry and other relatively expensive hardware, is not rendered permanently inoperative. With reference to FIG. 9, there is shown an embodiment of a single use/disposable electrode assembly, generally indicated by numeral 300. Assembly 300 permits permanent and irreversible disablement of a source of electrotransport current, the disablement effected by mechanical means in accordance with the present invention. The assembly 300 is provided with a mechanical and electrical fastener assembly, to be described below, which removably connects the electrode assembly 300 to an electrically conducting receiving cathode socket 302 and electrically conducting receiving anode socket 304 mounted in a reusable portion (not shown) of the electrotransport device. The sockets 302 and 304 are the supply nodes which provide the source of electrical current used by the detachable electrode assembly 300 to enable electrotransport delivery as described below.

The mechanical and electrical fastener assembly of electrode assembly 300 includes an electrically conducting cathode rivet 306 and an electrically conducting anode rivet 308. The cathode rivet 306 and anode rivet 308 are aligned to insert into the sockets 302 and 304 respectively. The sockets 302 and 304 are configured to receive and removably retain the respective cathode rivet 306 and the anode rivet 308 by means of conventional resilient spring members (not shown) or by means of an interference fit. The rivets 306 and 308 are configured to removably engage and be retained by the sockets 302 and 304 respectively.

The rivets 306 and 308 and the sockets 302 and 304 respectively, form the first removable electrical connection part of the mechanical fastener assembly herein described. The rivets 306 and 308 may be made of a commercially available metal, such as a high grade stainless steel, or may preferably be made of a base metal such as brass or copper and be plated or coated with a silver layer sufficient to minimize problems with electro-corrosion. The rivets 306 and 308 may also be made from a noble metal such as gold, or platinum. Alternatively the rivets 306 and 308 may be made of an insulating material such as ABS copolymer or polystyrene, having a sufficient coating of an electrically conductive material, such as graphite, silver or a noble metal, to provide continuous conductivity over their outside surfaces.

An insulating layer 314 is disposed between the rivets 306 and 308 and a second substrate layer 338. Layer 314 is preferably a thin, stretchable and tearable material such as polyethylene or polyurethane about 0.01 to 0.08 mm (0.05 to 3 mils) thick.

A layer 338 is affixed against the layer 314 opposite the rivets 306, 308. An adhesive layer (not shown) may be used to hold the layers 314 and 338 together at their areas of contact.

The layer 338 is preferably comprised of a foamed insulating material such as polyethylene or urethane foam about 0.3 to 7 mm (10 to 250 mils) thick. The layers 314 and 338 are preferably flexible enough to conform to normal body contours when applied as described below. The second layer 338 is provided with spaced apart cavities 340 and 344, one cavity 340 containing an anode gel reservoir 342 and another cavity 344 containing a cathode gel reservoir 346. One of the reservoirs 342 and 346 contains a therapeutic drug or agent and the other reservoir typically contains an electrolyte salt.

The layer 338 also has an open cavity 358 therethrough, the layer 338 being configured to separate the cavity 358 from the cavities 340 and 344. The cavity 358 is configured and aligned to encompass the studs 328 and 330 therein.

An anode electrode 334 is disposed between layer 314 and layer 338. The electrode 334 is sized and aligned to be in contact with a substantial portion of the anode gel reservoir 342. A cathode electrode 336 is disposed similarly between layer 314 and layer 338 and sized and aligned to be in contact with the cathode gel reservoir 346. The electrodes 334 and 336 are preferably made from a thin conducting material, such as a metallic (eg, silver anode or chloridized silver cathode) foil, a thin material having an electrically conductive surface, eg a polyethylene film having a metal or graphite coated surface, or a polymeric composite containing electrically conductive fillers such as that disclosed in U.S. Pat. No. 5,147,297 by Myers, et al, herein incorporated by reference. The composite may be extruded or rolled into a thin sheet form and then cut or stamped to the desired electrode shape.

The electrodes 334 and 336 have respective extended anode terminal 320 and cathode terminal 322 overlapping the open cavity 358. The terminals 320 and 322 form the input nodes of the electrode assembly 300 for conducting electrotransport current to the respective anode and cathode gel reservoirs 342, 346. The anode terminal 320 is aligned with an anode rivet socket 312 provided on the bottom of the anode rivet 308. The cathode terminal 322 is aligned with a cathode rivet socket 310 provided on the bottom of cathode rivet 306.

An anode stud 328 is aligned with the anode rivet socket 312. A cathode stud 330 is aligned with the cathode rivet socket 310. The studs 328 and 330 are provided with respective anode post 348 and cathode post 350. The studs 328 and 330 are preferably made of the same material as the rivets 306, 308, ie, silver plated steel, brass, or copper. The sockets 312 and 310 are configured to receive and retain the respective posts 348 and 350 when the posts are inserted through the respective openings 324, 326 and the layer 314 into the respective sockets. The rivet and post pairs 312, 348 and 310, 350 are configured to capture the respective electrode terminals 320 and 322 therebetween. The conductive outside surfaces of the rivets 310, 312 and the studs 328, 330 provide a continuous conducting contact between the terminals 320, 322 and the sockets 302, 304 respectively.

The studs 328, 330 and rivet sockets 312, 310 form the second electrical connecting part of the mechanical fastener assembly herein described.

A stud insulating layer 356 is preferably provided between the stud base 352 and stud base 354 and the body of the patient 360. Layer 356 isolates the patient's skin 360 from direct contact with the metal studs 328, 330 to prevent unwanted transfer of metallic ions into the skin 360.

An electrically conducting frangible member 332 between the anode terminal 320 and the anode electrode 334 forms a continuous conduction path therebetween. The term "frangible", as used in connection with member 332, means that the member breaks apart into physically separate portions when electrode assembly 300 is pulled away from the reusable portion of the electrotransport device. The term "frangible" specifically excludes electrically conductive coatings which are adapted to be scraped away, since the reliability of breaking an electrical connection by the action of scraping an electrically-conductive coating from a non-conducting substrate is not high. Thus, the term "frangible" only encompasses those electrically conducting members which are broken by physical separation of heretofore connected portions thereof.

The frangible member 332 can be a continuous extension of the electrode material 334. The frangible member 332 is preferably made from a conducting material having preformed grooves, scribes or perforations therein, such grooves, scribes or perforations configured to provide a weakened region for breaking and physical separation thereof when subjected to sufficient lateral force between the terminal 320 and the electrode 334.

In preparation for use, the studs 328, 330 are mounted into the rivets 308, 306, thereby capturing the respective terminals 320, 322 therebetween.

In use, the electrode assembly 300 is aligned with the reusable portion of the electrotransport device (not shown) having sockets 302, 304. The rivets 306, 308 are inserted into the respective anode socket 304 and cathode socket 302. The complete electrotransport device, including the reusable portion and the single use/disposable electrode assembly 300, is then applied to the patient's skin 360 and the electrotransport treatment begins with delivery of electrotransport current from the power supply to the electrodes 334, 336 in contact with the gel reservoirs 342, 346.

The supply node sockets 302, 304, the rivets 306, 308 and the studs 330, 328 are adapted to provide firm, but not permanent retention under extraction force caused by removing the disposable electrode assembly 300. The retention is sufficient to retain the electrode terminals 320, 322 between the rivets 306, 308 and studs 328, 330 when the electrode assembly 300 is removed from the reusable part of the electrotransport device.

At the end of the desired treatment, the power source and the assembly 300 are removed from the patient's skin 360. The electrode assembly 300 is removed from the reusable portion of the electrotransport device by pulling the layers 314 and 338 away therefrom. The studs 328, 330 remain inserted into the rivets 308, 306, and the rivets 306, 308 remain inserted into the sockets 302, 304. The frangible member 332 breaks into physically separate portions as the layers 314, 338 are pulled away, thereby permanently and irreversibly disabling the electrode assembly 300. Preferably, the frangible member 332 breaks apart internally without leaving studs 328, 330 and rivets 308, 306 attached to sockets 304, 302, respectively, thereby causing the electrode assembly 300 to be subsequently unusable with the same or another reusable portion of an electrotransport device. Alternatively, the terminal 320, as well as the stud 328 and the rivet 308, remain attached to the socket 304 once the electrode assembly 300 is disconnected from the reusable portion of the electrotransport device, thereby permanently and irreversibly breaking the electrical connection between socket 304 and electrode 334. The rivets 306, 308 may then be removed from the sockets 302, 304 by hand or by a small tool such as a screwdriver. Removing the rivets 306, 308 from the sockets 302, 304 in the reusable portion of the electrotransport device allows the reusable portion to be connected to a fresh single use/disposable electrode assembly 300 for further use.

It is also contemplated that different configurations of fastener assemblies and electrode assemblies are possible within the scope and spirit of this invention. For example, "Tinnerman" nuts may be used to retain posts which are configured to insert into sockets provided in the reusable portion of the device, removable retaining clips may be used for clamping the electrode terminals to power source connectors having the form of tabs.

Figure 10:
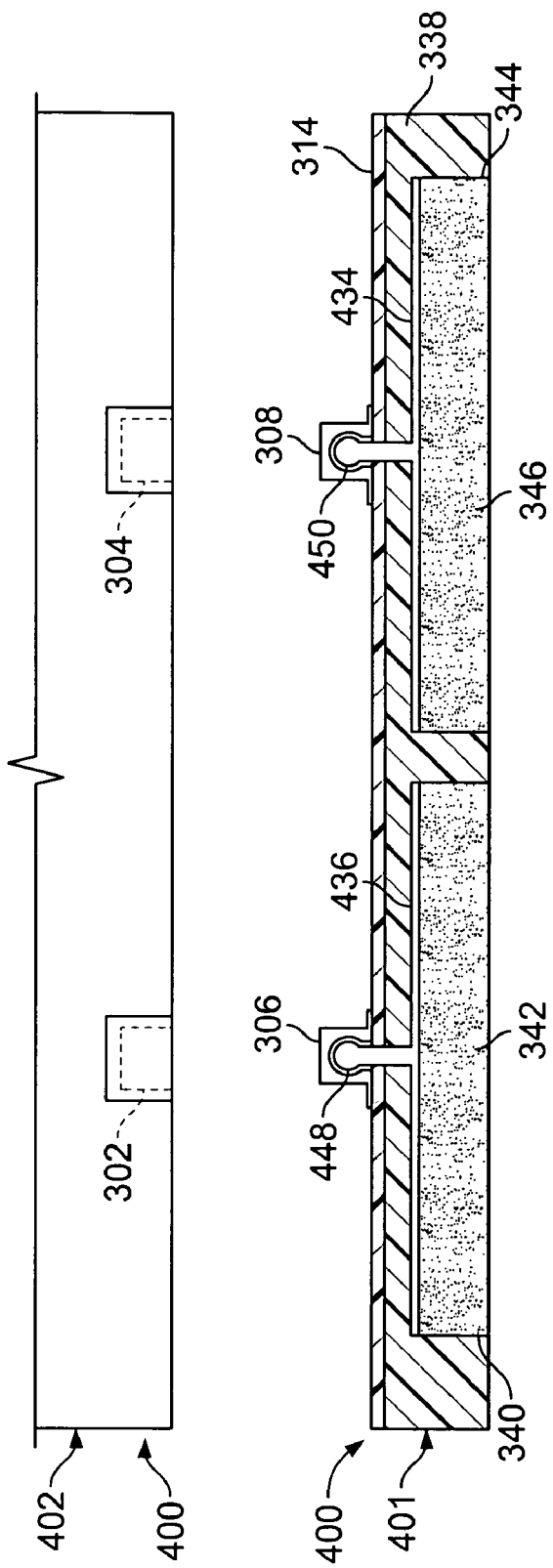
FIG. 10 is a side sectional view of a disposable/single use electrode assembly having electrodes comprised of a non-conductive material having an oxidizable/reducible electrically conductive coating.

Disablement of Electrotransport Current by Electrochemical Consumption of Conducting Member Referring now to FIG. 10, there is shown an electrotransport delivery device 400 comprised of a single use/disposable electrode assembly 401 and a reusable part 402. Like the device shown in FIG. 9, the reusable part 402 has sockets 302, 304 which are adapted to accept rivets 306, 308 in order to mechanically and electrically connect the disposable/single use electrode assembly 401 to the reusable part 402.

Similar to the single use/disposable electrode assembly 300 shown in FIG. 9, the single use/disposable electrode assembly 401 also includes an insulating layer 314 and a foam layer 338 having cavities 342, 344 therein. Cavities 340 and 344 are filled with gel reservoirs 342 and 346, respectively. At least one of the gel reservoirs 342 and 346 contains the therapeutic agent to be delivered by the device. Alternatively, reservoirs 342 and 346 may be in the form of a sponge or a fibrous material which can absorb a liquid solution of a drug or an electrolyte salt.

Unlike electrode assembly 300 shown in FIG. 9, electrode assembly 401 includes a pair of current distributing members 434, 436 disposed over the gels 346, 342, respectively. Electrode 434 includes a post 450 which is adapted to mate with rivet 308. Similarly, electrode 436 includes a post 448 which is adapted to mate with rivet 306. Electrodes 434, 436 and post 448, 450 are all composed of an electrically non-conductive material such as ABS copolymer or polystyrene. Electrodes 434, 436 and post 448, 450 are then coated with an electrically conductive material in order to impart electrical conductance to these members.

In accordance with this embodiment of the present invention, electrodes 434 and 436 are coated with a predetermined amount of a material which is (1) electrically conductive and (2)(i) in the case of an anode, either consumed by electrochemical oxidation or electrochemically oxidized to form a material which is electrically non-conductive; or (2)(ii) in the case of a cathode, either consumed by electrochemical reduction or electrochemically reduced to form a material which is electrically non-conductive. A material which is or becomes electrically "non-conductive" or a "resistor" as those terms are used herein means that the electrochemical conversion of the anodic and/or cathodic coating material yields an electrode which is at least five times more resistive, and preferably at least 10 times more resistive, than the resistance (R) calculated by dividing the maximum output voltage ($V_{max}$) of the power source/electrical controller by the desired output current (I) applied by the device (ie, $R=V_{max}/I$).

The electrically conductive coating on the anodic electrode is preferably an oxidizable metal such as zinc, silver, tin, copper or iron. The conductive coating material may also be an intercalation compound which is electrochemically oxidized to form a non-conductive material, e.g., sodium tungstate. Of these coating materials, silver is most preferred.

Suitable electrically conductive coatings for the cathodic electrode include intercalation compounds, such as electrically conductive polymers which, when electrochemically reduced, form a non-conductive material. Examples of these intercalation compounds include polypyrrole and polyaniline, both conductive polymers, and irridium oxide.

In operation, the disposable/single use electrode assembly 401 is connected to the reusable part 402 and the device is applied to a patient's body surface (eg, skin). Once applied to the patient, the device applies current through the sockets 302, 304; the rivets 306, 308; the post 448, 450; the electrodes 436, 434; the ion-containing gels 342, 346; and the patient's body. As current is carried from anodic electrode 434 to gel 346 containing an electrolyte medium (eg, an aqueous solution), electrochemical oxidation takes place at the interface between electrode 434 and gel 346. This interface is comprised of a coating of predetermined thickness of an oxidizable material such as silver. In time, more and more of the silver coating on electrode 434 is oxidized to form ions which migrate into gel 346. Eventually, substantially the entire coating of silver on electrode 434 is consumed by this oxidation process leaving only the bare ABS copolymer/polystyrene substrate which is electrically non-conductive. At this point, the electrical circuit between the part 402 and the gel 346 is permanently and irreversibly broken and the single use/disposable electrode assembly 401 is rendered permanently disabled. Alternatively, the oxidized silver ions may react with chloride ions present in gel 346 to form a silver chloride coating on the ABS substrate. Since silver chloride has a very low electrical conductivity, the formation of the silver chloride coating layer renders electrode assembly 401 non-conductive and permanently disabled.

As an alternative to, or in conjunction with, the oxidizable metallic coating on anodic electrode 434, cathodic electrode 436 may be coated with a predetermined amount of an electrochemically reducible material (e.g., polypyrrole) which, upon electrochemical reduction, forms an electrically insulating material. As current is applied from cathodic electrode 436 to gel 432, electrochemical reduction takes place at the interface. The interfacial surface of electrode 436 is comprised of the coating layer of polypyrrole. During application of current, the polypyrrole is electrochemically reduced. In its reduced form, polypyrrole is electrically non-conductive. Eventually, all of the polypyrrole is electrochemically reduced and the cathodic electrode 436 becomes electrically non-conductive. At this point, the disposable/single use electrode assembly 401 is rendered permanently and irreversibly disabled.

Those skilled in the art will appreciate that the amount of the coating of electrochemically oxidizable/reducible material provided on electrode 434 and/or electrode 436 can be calculated in accordance with the desired operating life of the electrode assembly 401. For example, if electrode assembly 401 is adapted to operate for a total of 25 mA·hrs, which is equivalent to 90 coulombs of current, then the amount of electrically conductive and oxidizable/reducible coating provided on electrode 434 or 436 may be calculated using Faraday's law. In accordance with Faraday's law, it takes 96,487 coulombs of electricity to liberate one gram-equivalent of material by oxidation or reduction. Accordingly, 90/96,487 or $9.3\times10^{-4}$ gram-equivalents of material are oxidized or reduced with the application of 90 coulombs of current. Thus, the coating of, eg silver on the anodic electrode or polypyrrole on the cathodic electrode should provide about $9.3\times10^{-4}$ gram-equivalents in order to ensure that the device will disable after application of 25 mA·hrs of current. The conversion of gram-equivalents to grams is well known to those of ordinary skill in the chemical arts. For example, $9.3\times10^{-4}$ gram-equivalents of silver is equal to 0.10 g silver (ie, ($9.3\times10^{-4}$ gram-equivalents Ag)×(108 g Ag/mole Ag)×(1 mole Ag/gram-equivalent Ag)=0.10 g Ag).

As an alternative to using electrodes 434, 436 and post 448, 450 comprised of an electrically non-conductive material which is coated with an electrically conductive coating, electrodes 434, 436 and post 448, 450 can also be made from an electrically conductive material which is neither oxidizable nor reducible. Suitable materials include stainless steel, platinum, gold and carbon. Such materials are then coated with a predetermined amount of an electrochemically oxidizable material on the anodic electrode, and/or an electrochemically reducible material on the cathodic electrode, as described before. Suitable electrochemically oxidizable and reducible materials which can be coated on an electrically conductive substrate include those materials described in Untereker et al. U.S. Pat. No. 5,135,477, which is incorporated herein by reference. Of these materials, oxidizable silver and reducible silver chloride are most preferred. When the oxidizable/reducible materials are consumed, there is a measurable increase in the voltage required to maintain the flow of current between the electrode 434 and gel 346 and/or between electrode 436 and gel 342. Although, the resistance does not increase as dramatically as in the previous embodiment utilizing electrodes and posts made of non-conductive polymers, the voltage change is measurable and hence a voltage sensor (not shown) using a reference electrode (not shown) located within gel 342 and/or gel 346 can sense when the oxidizable/reducible coating material is consumed, causing the voltage drop to increase. Such a sensor can be conventionally connected to the electronic circuit powering the device so as to generate a disabling signal which is effective to disable the current output of the current generating circuit 24 as described hereinbefore. Alternatively, the total voltage required to maintain the current can be measured by electronic circuit 24 and a disabling mode can be activated when a predetermined rise, or a predetermined rate of rise in the total voltage occurs due to the oxidation and/or reduction of the coating material. This alternative embodiment has the advantage of not requiring a reference electrode.

Most preferably, an electrotransport device which is permanently disabled by electrochemical consumption of a conducting member is also provided with either a timer (i.e., in the case of an electrotransport device which applies a constant level of current) or a current integrator (i.e., in the case of an electrotransport device which applies a level of current which varies over time). The timer or current integrator may be set to operate in a manner similar to the operation of timer 66 illustrated in FIG. 1. The timer is set to run for a predetermined period of time (e.g., 24 hours) which may correspond to the recommended wearing time for the device. The timer then turns the device off after the predetermined period of time has elapsed. Alternatively, in the case of the current integrator, the integrator turns the device off after a predetermined amount of charge has been applied by the device.

Most preferably, the timer/current integrator is part of a reusable controller portion of a two-part electrotransport device. In such a device, the timer/current integrator is capable of being reset each time a new single/disposable portion (e.g., assembly 300 shown in FIG. 9) is attached to the reusable controller portion of the device. Alternatively, the timer/current integrator may be reset automatically after a predetermined amount of time (eg, a lock-out period) has elapsed after termination of treatment. In such a device, the timer/current integrator acts as a primary means for preventing use of the disposable portion after the expiration of a set period of time (e.g., 24 hours) or upon application of a predetermined amount of charge, in the case of the current integrator. The electrochemically consumable coating material acts as a secondary, or backup, means for preventing unauthorized use of the single use/disposable component beyond its intended useful life. Most preferably, the timer/current integrator is set to signal the controller to turn itself off just prior to complete consumption of the electrochemically reactive coating.

It is contemplated that the various embodiments of the invention may be combined in various combinations to provide, for example, an embodiment combining the effects of the system described with respect to FIG. 1 and that described with respect to FIG. 2, or a combination of the various devices depicted in the drawings and described above.

While the foregoing detailed description has described the embodiments of the permanent and irreversible disabling electrotransport device in accordance with this invention, it is to be understood that the above description is illustrative only and not limiting of the disclosed invention. It will be appreciated that it is possible to modify the number and type of disablement circuits, the materials and methods of construction and the logic forms and interconnections or to include or exclude various elements within the scope and spirit of the invention. Thus the invention is to be limited only by the claims as set forth below.

What is claimed is:

1. An electrotransport device for delivering a therapeutic agent, comprising:
   a power source;
   first and second electrodes and reservoirs, wherein at least one of the reservoirs contains the therapeutic agent;
   a current generating circuit;
   a current controlling circuit;
   a current enabling circuit;
   a current disabling circuit adapted to automatically, permanently and irreversibly disable the current generating circuit upon occurrence of a predetermined event, thereby discontinuing electrotransportation of the agent from the device, said current disabling circuit including a timer circuit, wherein said predetermined event is the expiration of a period of time establishing by said timer circuit; and
   a current discharging circuit including a silicon controlled rectifier or a field effect transistor.

2. The device of claim 1, wherein said period of time is from initiation of said timer circuit to a shelf-life.

3. The device of claim 1, wherein the therapeutic agent comprises an abusable drug.

4. The device of claim 3, wherein the abusable drug is a narcotic analgesic.

5. The device of claim 3, wherein said abusable drug is a member selected from the group consisting of fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine.

6. The device of claim 1, wherein the timer circuit can be set to after a predetermined period of time fire a silicon controlled rectifier to discharge a battery to permanently and irreversibly disable the current generating circuit.

7. The method of claim 6, wherein the silicon controlled rectifier is connected to a resistor to discharge the battery.

8. A method of delivering a therapeutic agent by electrotransport, comprising the steps of:
   providing an electrotransport device for delivering a therapeutic agent comprising:
   a power source; first and second electrodes and reservoirs, wherein at least one of the reservoirs contains the therapeutic agent; a current generating circuit; a current controlling circuit; a current enabling circuit; a discharging circuit including a silicon controlled rectifier or a field effect transistor and a current disabling circuit including a timer circuit adapted to automatically, permanently and irreversibly disable the current generating circuit upon occurrence of a predetermined event, thereby discontinuing electrotransportation of the agent from the device; and
   automatically, permanently, and irreversibly disabling the current generating circuit upon the occurrence of a predetermined event, thereby discontinuing electrotransportation of the agent from the device.

9. The method of claim 8, wherein said predetermined event comprises the expiration of the shelf-life of the device.

10. The method of claim 8, wherein the timer circuit can be set to after a predetermined period of time fire a silicon controlled rectifier to discharge a battery to permanently and irreversibly disable the current generating circuit.

11. An electrotransport device for delivering a therapeutic agent, comprising:
   a power source;
   first and second electrodes and reservoirs, wherein at least one of the reservoirs contains the therapeutic agent;
   a current generating circuit;
   a current controlling circuit;
   a current enabling circuit; and
   current disabling means adapted to automatically, permanently and irreversibly disable the current generating circuit upon occurrence of a predetermined event, thereby discontinuing electrotransportation of the agent from the device, said disabling means including a timer, wherein said disabling means is activated after said timer measures a predetermined period of time.

12. The device of claim 11, wherein said timer is activated when said current generating circuit is first placed in operation.

13. The device of claim 11, wherein said tinier is activated when the electrotransport device is manufactured.

14. The device of claim 11, wherein the agent comprises an abusable drug.

15. The device of claim 14, wherein said abusable drug comprises a narcotic analgesic.

16. The device of claim 14, wherein said abusable drug is selected from the group consisting of fentanyl, sufentanil, carfentanil, lofentanil, alfentanil, hydromorphone, oxycodone, propoxyphene, pentazocine, methadone, tilidine, butorphanol buprenorphine, levorphanol, codeine, oxymorphone, meperidine, dihyrocodcinone and cocaine.

17. The device of claim 11, wherein the timer circuit can be set to after a predetermined period of time fire a silicon controlled rectifier to discharge a battery to permanently and irreversibly disable the current generating circuit.

* * * * *